United States Patent
Wang et al.

(10) Patent No.: US 9,952,130 B2
(45) Date of Patent: Apr. 24, 2018

(54) JIG FOR DROPPING BALL TEST

(71) Applicants: BOE Technology Group Co., Ltd., Beijing (CN); Hefei Xinsheng Optoelectronics Technology Co., Ltd., Anhui (CN)

(72) Inventors: Qingpu Wang, Beijing (CN); Ming Hu, Beijing (CN); Taofeng Xie, Beijing (CN)

(73) Assignees: BOE TECHNOLOGY GROUP CO., LTD., Beijing (CN); HEFEI XINSHENG OPTOELECTRONICS TECHNOLOGY CO., LTD., Anhui (CN)

( * ) Notice: Subject to any disclaimer, the term of this patent is extended or adjusted under 35 U.S.C. 154(b) by 48 days.

(21) Appl. No.: 14/742,853

(22) Filed: Jun. 18, 2015

(65) Prior Publication Data

US 2016/0084745 A1   Mar. 24, 2016

(30) Foreign Application Priority Data

Sep. 23, 2014  (CN) .......................... 2014 1 0491648

(51) Int. Cl.
   *G01N 3/303*   (2006.01)
(52) U.S. Cl.
   CPC ................... *G01N 3/303* (2013.01)
(58) Field of Classification Search
   CPC .... G01N 3/303; G01N 3/30; G01N 2203/001; G01N 2033/0078; G01N 2033/008
   USPC ................. 73/844, 856, 12.01–12.14, 78–85
   See application file for complete search history.

(56) References Cited

U.S. PATENT DOCUMENTS

| | | | |
|---|---|---|---|
| 2003/0226404 A1* | 12/2003 | Ouellet | G01N 3/20 73/849 |
| 2006/0000306 A1* | 1/2006 | Schmitt | F16M 11/12 74/490.07 |
| 2010/0162789 A1* | 7/2010 | Su | G01N 3/303 73/12.06 |

(Continued)

FOREIGN PATENT DOCUMENTS

| | | |
|---|---|---|
| CN | 202057470 U | 11/2011 |
| CN | 102829943 A | 12/2012 |

(Continued)

OTHER PUBLICATIONS

First Office Action, including Search Report, for Chinese Patent Application No. 201410491648.3, dated Mar. 28, 2016, 11 pages.

*Primary Examiner* — Hezron E Williams
*Assistant Examiner* — Marrit Eyassu
(74) *Attorney, Agent, or Firm* — Westman, Champlin & Koehler, P.A.

(57) ABSTRACT

The present invention relates to a field of display technology, in particular, to a jig for dropping ball test. The jig for dropping ball test comprises a fixing device and a dropping ball device. The fixing device comprises a plurality of adjusting rods for fixing a sample to be tested, a test region corresponding to the shape of the sample to be tested is enclosed by the plurality of adjusting rods. The dropping ball device is used to drop a ball towards the sample to be tested. The fixing device of the jig can be adjusted in its size according to the size of a sample to be tested, so that the dropping ball test can be carried out for different samples, which is easy to operate and reduces manufacturing cost.

8 Claims, 2 Drawing Sheets

(56) References Cited

U.S. PATENT DOCUMENTS

2012/0186359 A1* 7/2012 Huang ................ G01M 99/007
73/856
2013/0169590 A1* 7/2013 Wickboldt ............. G02B 1/105
345/174
2013/0213113 A1* 8/2013 Huang .................... G01M 7/08
73/12.13

FOREIGN PATENT DOCUMENTS

| CN | 102840958 A | | 12/2012 |
|----|----|----|----|
| CN | 202765830 U | | 3/2013 |
| CN | 103257025 A | | 8/2013 |
| CN | 204154466 U | * | 2/2015 |
| JP | H06-29362 A | | 2/1994 |
| KR | 10-2013-0107679 A | | 10/2013 |

* cited by examiner

JIG FOR DROPPING BALL TEST

CROSS-REFERENCE TO RELATED APPLICATION

This application claims the benefit of Chinese Patent Application No. 201410491648.3 filed on Sep. 23, 2014 in the State Intellectual Property Office of China, the whole disclosure of which is incorporated herein by reference.

BACKGROUND OF THE INVENTION

Field of the Invention

The present invention relates to a field of display technology, in particular, to a jig for dropping ball test.

Description of the Related Art

At present, there is a risk to be dropped or impacted for a touch screen of smartphone and tablet PC. In order to test a structural strength of the touch screen, the manufacturer typically applies an impact test to the touch screen before shipment. A general method is to drop steel balls with different weight at different heights and then impact on the touch screen, obtaining related impact data to make a judgment. A test with this function is often referred as a dropping ball test, which may be applied to consumer electronics such as cellphone, tablet PC, LCD, cover glass, glass lens and resin lens, etc.

An existing system for dropping ball test typically comprises a part for releasing the dropping ball and a part for fixing a sample. The part for releasing the dropping ball is located above the part for fixing a sample to drop a ball towards a sample to be tested, and the part for fixing a sample is used to fix the sample to be test. However, the part for fixing a sample of the existing system for dropping ball test is not allowed to be adjusted in its size according to the size of the sample to be tested, thus, one set of corresponding fixing jig is required for each version of touch screen, that is, it is impossible for one set of fixing jig to correspond to different samples to carry out the dropping ball test.

Due to the above disadvantages, a jig which is able to carry out the dropping ball test with regard to different samples is needed.

SUMMARY OF THE INVENTION

The present invention aims to solve a technical problem existing in the prior art which is how to carry out the dropping ball test for different samples.

In order to solve the above technical problem, the present invention provides a jig for dropping ball test comprising a fixing device and a dropping ball device, wherein the fixing device comprises a plurality of adjusting rods for fixing a sample to be tested, a test region corresponding to the shape of the sample to be tested is enclosed by the plurality of adjusting rods, the dropping ball device is used to drop a ball towards the sample to be tested.

Further, the present invention provides a fixing device, the fixing device comprises a plurality of adjusting rods for fixing a sample to be tested, a test region corresponding to the shape of the sample to be tested is enclosed by the plurality of adjusting rods, the test region is allowed to be varied in its size as the adjusting rods move so as to be adapted to different sizes of the sample to be tested.

Wherein, each of adjusting rods comprises a rod body and a slider, a sliding rail is disposed on the rod body, the slider is located at an end of the sliding rail; the plurality of adjusting rods are connected end to end in succession, a receiving space for chucking the sample to be tested is formed inside the adjusting rods, and the slider of each adjusting rod is located on the sliding rail of another adjusting rod connected therewith.

Wherein, the adjusting rods comprises a first adjusting rod, a second adjusting rod, a third adjusting rod and a fourth adjusting rod, the slider of the first adjusting rod is located on the sliding rail of the second adjusting rod to slide in an axial direction of the second adjusting rod, the slider of the second adjusting rod is located on the sliding rail of the third adjusting rod to slide in an axial direction of the third adjusting rod, the slider of the third adjusting rod is located on the sliding rail of the fourth adjusting rod to slide in an axial direction of the fourth adjusting rod, the slider of the fourth adjusting rod is located on the sliding rail of the first adjusting rod to slide in an axial direction of the first adjusting rod.

Wherein, a groove with a downward opening is disposed in the slider.

Wherein, the sliding rail protrudes from an outside of the rod body and the receiving space is located inside of the rod body.

Wherein, a scratch-resistant layer is provided on the receiving space.

Wherein, the material of the scratch-resistant layer is plastic or rubber.

Wherein, the dropping ball device comprises a releasing device and a liftable support, the releasing device is located above the fixing device by the liftable support, and a ball is dropped by the releasing device and impacts on the sample to be tested.

The technical solutions of the present invention have following beneficial effects: the fixing device is designed to be adjustable in the jig for dropping ball test of the present invention, the fixing device comprises a plurality of adjusting rods for fixing a sample to be tested, a test region corresponding to the shape of the sample to be tested is enclosed by the plurality of adjusting rods, the test region is allowed to be adjusted in its size according to the size of the sample to be tested, so that the dropping ball test can be carried out for different samples, the operation is convenient and the manufacture cost is effectively reduced.

LIST OF REFERENCE NUMERALS

Figure 1:
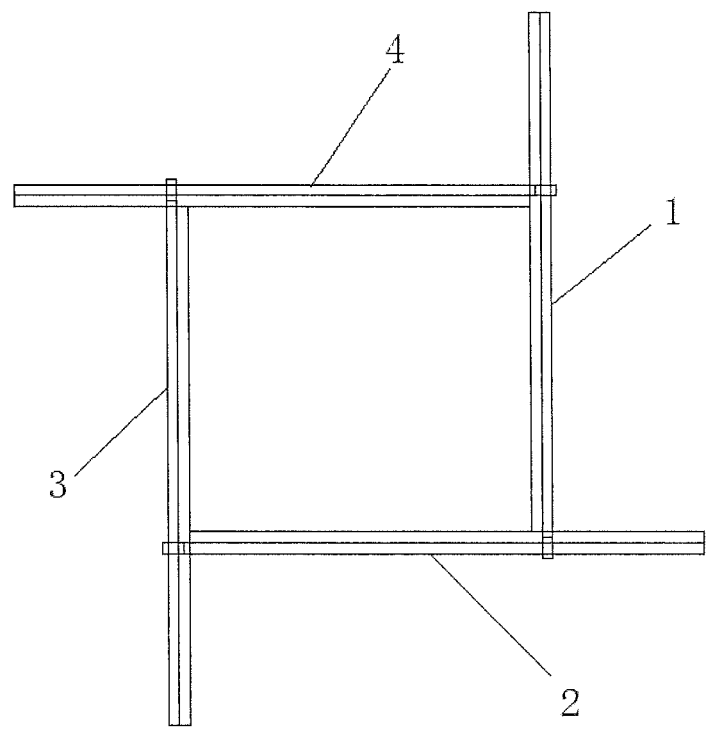
FIG. 1 is a structural schematic view of a fixing device according to an embodiment of the present invention.

1: first adjusting rod; 2: second adjusting rod; 3: third adjusting rod; 4: fourth adjusting rod; 5: rod body; 6: slider; 7: sliding rail.

DETAILED DESCRIPTION OF PREFERRED EMBODIMENTS OF THE INVENTION

Implementations of the present invention will be described further in detail in the following in combination with drawings and preferable embodiments. The following embodiments is only used to explain the present invention, but not used to limit the scope of the present invention.

In the description of the present invention, except as otherwise noted, a term such as "a plurality of", "multiple", "several" means two or more. An orientation, direction or position indicated by a directional term such as "up", "down", "left", "right", "in", "out", "front", "rear", "head", "tail" is based on the orientation, direction or position as shown in the drawings, and it is only for purpose of a convenient and simplified description of the present invention, rather than indicate or imply that a device or element indicated by them has to possess the specific orientation, direction or position or to be configured or operated in the specific orientation, direction or position, that is, these directional terms should not interpreted as limiting the present invention. Moreover, a term such as "first", "second", "third" is only for purpose of description and should not interpreted as indicating or implying relative importance.

It should be noted that in the description of the present invention, except as otherwise specific rule or definition, a term such as "mount", "connect", "attach" should be understood in a broad sense, for example, it may be a fixed connection, a removable connection, an integral connection, a mechanical connection, a direct connection, or an indirect connection through a bridge part. Those skilled in the art may understand its specific meaning according to a specific context in the present invention.

The jig for dropping ball test provided by an embodiment of the present invention comprises a fixing device and a dropping ball device. The fixing device comprises a plurality of adjusting rods for fixing a sample to be tested, a test region corresponding to the shape of the sample to be tested is enclosed by the plurality of adjusting rods, the plurality of adjusting rods are movable to each other to realize the fixing of different samples to be test. The dropping ball device is positioned above the fixing device for dropping balls to the sample to be tested. Balls (iron ball or steel ball) with different weight can be dropped from different heights and impact the sample to be tested, so that data associated with the impact is obtained to make a further judgment.

Figure 2:
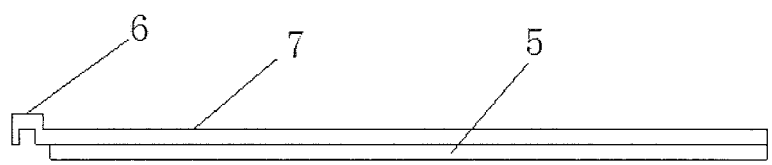
FIG. 2 is a front view of adjusting rods according to an embodiment of the present invention.

As shown in FIG. 2, in the embodiment, each of the plurality of adjusting rods comprises a rod body 5 and a slider 6, a sliding rail 7 is disposed on the rod body 5 in an axial direction thereof. The slider 6 is located at an end of the sliding rail 7. The plurality of adjusting rods are connected end to end in succession, and a receiving space for chucking and fixing the sample to be tested is formed inside the adjusting rods. And the slider 6 of each adjusting rod is located on the sliding rail 7 of another adjusting rod connected therewith. With regard to the slider 6 and the sliding rail 7, the slider 6 of the first adjusting rod 1 is movably connected to the sliding rail 7 of the second adjusting rod 2; the slider 6 of the second adjusting rod 2 is movably connected to the sliding rail 7 of the third adjusting rod 3; the slider 6 of the third adjusting rod 3 is movably connected to the sliding rail 7 of the fourth adjusting rod 4; the slider 6 of the fourth adjusting rod 4 is movably connected to the sliding rail 7 of the first adjusting rod 1.

Figure 3:
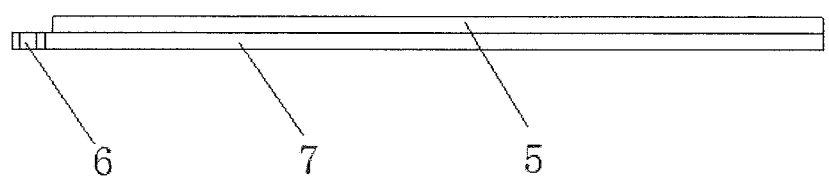
FIG. 3 is a plan view of adjusting rods according to an embodiment of the present invention.
Figure 4:
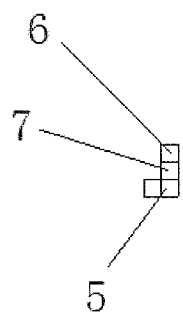
FIG. 4 is a side view of adjusting rods according to an embodiment of the present invention.

In the embodiment, the test region is located inside the receiving space for the dropping ball test. As shown in FIG. 3-4, the sliding rail 7 protrudes from the outside of the rod body 5 and the width of the sliding rail 7 is less than that of the rod body 5, as a result, a recessed space is enclosed at the rod body 5 and one side of the sliding rail 7 inside the rod body 5, that is, the receiving space. Practically, other snap groove structures for fixing the sample to be tested inside the rod body 5 also fall into the scope of the present embodiment. The receiving space is allowed to be varied in its size as the adjusting rods move so as to adapt to samples with different sizes.

As shown in FIG. 1, in the embodiment, the fixing device uses four adjusting rods which comprise a first adjusting rod 1, a second adjusting rod 2, a third adjusting rod 3 and a fourth adjusting rod 4. The first adjusting rod 1 slides in an axial direction of the second adjusting rod 2, that is, the slider 6 of the first adjusting rod 1 is connected on the sliding rail 7 of the second adjusting rod 2 and can slide left and right in the axial direction of the second adjusting rod 2. The second adjusting rod 2 slides in an axial direction of the third adjusting rod 3, that is, the slider 6 of the second adjusting rod 2 is connected on the sliding rail 7 of the third adjusting rod 3 and can slide up and down in the axial direction of the third adjusting rod 3. The third adjusting rod 3 slides in an axial direction of the fourth adjusting rod 4, that is, the slider 6 of the third adjusting rod 3 is connected on the sliding rail 7 of the fourth adjusting rod 4 and can slide left and right in the axial direction of the fourth adjusting rod 4. The fourth adjusting rod 4 slides in an axial direction of the first adjusting rod 1, that is, the slider 6 of the fourth adjusting rod 4 is connected on the sliding rail 7 of the first adjusting rod 1 and can slide up and down in the axial direction of the first adjusting rod 1.

Further, a groove with a downward opening is disposed in the slider 6 and positioned on the sliding rail 7. The slider 6 is positioned at one end of the sliding rail 7 and placed outside of the connecting rod, ensuring each part does not interfere with each other when adjusted.

In the embodiment, the test region corresponding to the shape of the sample to be tested is formed by the plurality of adjusting rods. The sample to be tested may be a touch screen for smartphone and tablet computer, or also may be other components. In order to prevent the fixing device from scratching the touch screen to be tested, a scratch-resistant layer may be provided at sides of the rod body 5 and the sliding rail 7 in the receiving space, respectively. Wherein, the scratch-resistant layer may be a plastic or rubber coated on the rod body 5. Certainly, each of the adjusting rods of the fixing device may also be made from a material with higher flatness such as wood.

It should be noted that, there are four adjusting rods in the embodiment, a rectangle test region with any size may be enclosed by the four adjusting rods, this arrangement is designed for rectangle samples to be tested. As for samples with other shapes, the number and shape of the adjusting rods may be flexibly set on the basis of the structure in the embodiment.

In addition, in the embodiment, the dropping ball test jig further comprises a dropping ball device. And Balls (iron ball or steel ball) with different weight can be dropped from different heights by the dropping ball device and impact the sample to be tested. The fixing device can be used cooperatively with any dropping ball device capable of dropping balls to the sample to be tested.

Preferably, the dropping ball device comprises a releasing device and a liftable support. The releasing device is positioned above the fixing device through the liftable support, and the ball falls by the releasing device and impacts the sample to be tested.

In summary, in the dropping ball test jig of the embodiment, the fixing device is designed to be an adjustable one. The fixing device comprises a plurality of adjusting rods for fixing a sample to be tested, a test region corresponding to the shape of the sample to be tested is enclosed by the plurality of adjusting rods and can be adjusted in its size according to the size of a sample to be tested, so that the dropping ball test can be carried out for different samples, which is easy to operate and reduces manufacturing cost.

Embodiments of the present invention are given for purpose of illustration and description, rather than exhaustive or to limit the present invention to the disclosed forms. Many modifications and changes are obvious by those skilled in the art. Embodiments are chosen and described in order to better explain the principles and practice of the present invention and enable those skilled in the art to understand the invention, thus various embodiments suitable for a particular application with various modifications can be designed.

What is claimed is:

1. A jig for dropping ball test comprising a fixing device, wherein, the fixing device comprises a plurality of adjusting rods for fixing a sample to be tested, a test region corresponding to the shape of the sample to be tested is entirely enclosed by the plurality of adjusting rods, and the test region is allowed to be varied in its size as the adjusting rods move so as to be adapted to different sizes of the sample to be tested, and wherein, each of adjusting rods comprises a rod body and a slider, a sliding rail is disposed on the rod body, the slider is located at an end of the sliding rail; the plurality of adjusting rods are connected end to end in succession, and the slider of each adjusting rod is located on the sliding rail of another adjusting rod connected therewith, and a groove with a downward opening is disposed in the slider, to avoid dust and debris accumulation, the sliding rail protrudes from an outside of the rod body and a receiving space is located inside of the rod body.

2. The jig for dropping ball test of claim 1, wherein the adjusting rods comprises a first adjusting rod, a second adjusting rod, a third adjusting rod and a fourth adjusting rod, the slider of the first adjusting rod is located on the sliding rail of the second adjusting rod to slide in an axial direction of the second adjusting rod, the slider of the second adjusting rod is located on the sliding rail of the third adjusting rod to slide in an axial direction of the third adjusting rod, the slider of the third adjusting rod is located on the sliding rail of the fourth adjusting rod to slide in an axial direction of the fourth adjusting rod, the slider of the fourth adjusting rod is located on the sliding rail of the first adjusting rod to slide in an axial direction of the first adjusting rod.

3. The jig for dropping ball test of claim 1, wherein a scratch-resistant layer is provided on the receiving space.

4. The jig for dropping ball test of claim 3, wherein the material of the scratch-resistant layer is plastic or rubber.

5. The fixing device of claim 1, wherein a scratch-resistant layer is provided on the receiving space.

6. The fixing device of claim 5, wherein the material of the scratch-resistant layer is plastic or rubber.

7. A fixing device comprising a plurality of adjusting rods for fixing a sample to be tested, wherein a test region corresponding to the shape of the sample to be tested is entirely enclosed by the plurality of adjusting rods, and the test region is allowed to be varied in its size as the adjusting rods move so as to be adapted to different sizes of the sample to be tested, and wherein, each of adjusting rods comprises a rod body and a slider, a sliding rail is disposed on the rod body, the slider is located at an end of the sliding rail; the plurality of adjusting rods are connected end to end in succession, and the slider of each adjusting rod is located on the sliding rail of another adjusting rod connected therewith, and a groove with a downward opening is disposed in the slider, to avoid dust and debris accumulation, the sliding rail protrudes from an outside of the rod body and a receiving space is located inside of the rod body.

8. The fixing device of claim 7, wherein the adjusting rods comprises a first adjusting rod, a second adjusting rod, a third adjusting rod and a fourth adjusting rod, the slider of the first adjusting rod is located on the sliding rail of the second adjusting rod to slide in an axial direction of the second adjusting rod, the slider of the second adjusting rod is located on the sliding rail of the third adjusting rod to slide in an axial direction of the third adjusting rod, the slider of the third adjusting rod is located on the sliding rail of the fourth adjusting rod to slide in an axial direction of the fourth adjusting rod, the slider of the fourth adjusting rod is located on the sliding rail of the first adjusting rod to slide in an axial direction of the first adjusting rod.

* * * * *